(12) United States Patent
Schoennagel et al.

(10) Patent No.: US 10,442,824 B2
(45) Date of Patent: Oct. 15, 2019

(54) METHOD FOR THE PRODUCTION OF A TITANIUM CONTAINING CATALYST, TITANIUM CONTAINING CATALYST, METHOD FOR THE PRODUCTION OF POLYESTER AND POLYESTER

(71) Applicants: UHDE INVENTA-FISCHER GMBH, Berlin (DE); CATALYTIC TECHNOLOGIES LIMITED, London NW (GB)

(72) Inventors: Matthias Schoennagel, Berlin (DE); Alan Thomas Cooper, Wingate (GB)

(73) Assignees: UHDE INVENTA-FISCHER GMBH, Berlin (DE); CATALYTIC TECHNOLOGIES LIMITED, London NW (GB)

( * ) Notice: Subject to any disclaimer, the term of this patent is extended or adjusted under 35 U.S.C. 154(b) by 0 days.

(21) Appl. No.: 14/766,021

(22) PCT Filed: Jan. 31, 2014

(86) PCT No.: PCT/EP2014/051896
§ 371 (c)(1),
(2) Date: Oct. 14, 2015

(87) PCT Pub. No.: WO2014/122070
PCT Pub. Date: Aug. 14, 2014

(65) Prior Publication Data
US 2016/0108068 A1 Apr. 21, 2016

(30) Foreign Application Priority Data
Feb. 6, 2013 (EP) .................... 13154209

(51) Int. Cl.
*B01J 31/22* (2006.01)
*C08G 63/85* (2006.01)
*C08G 63/16* (2006.01)
*C07F 7/28* (2006.01)

(52) U.S. Cl.
CPC .............. *C07F 7/28* (2013.01); *C08G 63/16* (2013.01); *C08G 63/85* (2013.01); *B01J 31/223* (2013.01); *B01J 2531/46* (2013.01)

(58) Field of Classification Search
CPC ...... C08G 63/85; C08G 63/183; C08G 63/87; C08G 2261/1412; C08G 2261/3243; C08G 2261/344; C08G 2261/411; C08G 61/124; C08G 61/126; C08G 63/16; B01J 2531/46; B01J 31/0258; B01J 31/223; C07C 67/08; C07C 69/80; C07C 69/82; C07C 67/03
See application file for complete search history.

(56) References Cited

U.S. PATENT DOCUMENTS

| | | | |
|---|---|---|---|
| 2,071,250 A | 2/1937 | Carothers | |
| 2,465,319 A | 3/1949 | Whinfield et al. | |
| 4,356,299 A | 10/1982 | Cholod et al. | |
| 5,866,710 A * | 2/1999 | Ridland | C07C 67/03 554/170 |
| 6,080,834 A * | 6/2000 | Putzig | B01J 31/0212 502/103 |
| 6,559,271 B2 | 5/2003 | Schaaf et al. | |
| 7,094,863 B2 | 8/2006 | Moore et al. | |
| 7,144,974 B2 | 12/2006 | Honda et al. | |
| 7,368,522 B2 | 5/2008 | Jernigan et al. | |
| 7,544,762 B2 | 6/2009 | Yamamoto et al. | |
| 2004/0044173 A1 | 3/2004 | Fujimori et al. | |
| 2004/0266978 A1 | 12/2004 | Honda et al. | |
| 2007/0010648 A1 | 1/2007 | Partridge et al. | |
| 2011/0162205 A1 | 7/2011 | Kong et al. | |
| 2012/0088898 A1 | 4/2012 | Schoennagel | |
| 2012/0271030 A1* | 10/2012 | Lindall | B01J 31/04 528/278 |

FOREIGN PATENT DOCUMENTS

| CN | 1962737 | * | 5/2007 |
|---|---|---|---|
| CN | 1962737 A | | 5/2007 |

(Continued)

OTHER PUBLICATIONS

Joseph M. Collins et al. "Titanium(IV) Citrate Speciation and Structure under Environmentally and Biologically Relevant Conditions",Inorganic Chemistry, vol. 44, No. 10, 2005.*
E. T. Kefalas et alMononuclear Titanium(IV)-Citrate Complexes from Aqueous Solutions: pH-Specific Synthesis and Structural and Spectroscopic Studies in Relevance to Aqueous Titanium(IV)-Citrate Speciation Inorg Chem. 2005, 44,pp. 2596-2605.*
European Patent Office, International Search Report in International Application No. PCT/EP2014/051896 (dated Jul. 2, 2014).
State Intellectual Property Office of the People'S Republic of China, Notification of the First Office Action in Chinese Patent Application No. 201480007800.4 (dated Apr. 25, 2016).
Eurasian Patent Organization, Notification on Necessity of Presenting Additional Materisl in Eurasian Patent Application No. 201591046/28 (dated Jun. 21, 2016).

(Continued)

*Primary Examiner* — Ling Siu Choi
*Assistant Examiner* — Gennadiy Mesh
(74) *Attorney, Agent, or Firm* — Leydig, Voit & Mayer, Ltd.

(57) ABSTRACT

Disclosed is a method for producing a titanium containing catalyst, wherein the catalyst includes one or more titanium alpha-hydroxy carboxylate species, e.g., titanium citrate, and one or more titanium oxide species, e.g., $TiO_x$, wherein x is greater than 0 and less than or equal to 2, wherein the sum of all of the above titanium oxide species relative to the sum of all titanium alpha-hydroxy carboxylate species in the titanium containing catalyst is greater than 0 but less than 1.00 mol.-%. The method of production involves, for example, reacting tetraisopropyl orthotitanate with an aqueous solution of citric acid, and removing the byproduct of 2-propanol by distillation. Also disclosed is a method for the production of polyesters by the use of the catalyst.

6 Claims, 1 Drawing Sheet

(56) References Cited

FOREIGN PATENT DOCUMENTS

| | | |
|---|---|---|
| DE | 19506407 A1 | 8/1996 |
| EP | 1 013 692 A2 | 6/2000 |
| EP | 1 491 572 A1 | 12/2004 |
| EP | 2 006 315 A1 | 12/2008 |
| EP | 2 365 029 A2 | 9/2011 |
| TW | 200504114 A | 2/2005 |
| WO | WO 97/08223 A1 | 3/1997 |
| WO | WO 2004/050239 A2 | 6/2004 |
| WO | WO 2004/065452 A1 | 8/2004 |
| WO | WO 2006/001113 A1 | 1/2006 |
| WO | WO 2008/150350 A1 | 12/2008 |

OTHER PUBLICATIONS

Bradley, "Metal Alkoxides as Precursors for Electronic and Ceramic Materials," *Chemical Reviews, American Chemical Society 89*(6), pp. 1317-1322 (1989).

Cooney et al., "Thermal Degradation of Poly(ethylene Terephthalate)—A Kinetic Analysis of Thermogravimetric Data," *Journal of Applied Polymer Science 28*, pp. 2887-2902 (1983).

Ludewig, *"Polvesterfasern, Chemie and Technologie,"* ("Polyester Fibers—Chemistry and Technology") Akademie-Verlag, Berlin, pp. 132-139 (1975).

Tsay et al., "Effects of Molar Ratio of Citric Acid to Cations and of pH Value on the Formation and Thermal-Decomposition Behavior of Barium Titanium Citrate," *Journal of the American Ceramic Society 82*(6), pp. 1409-1415 (1999).

Wick, "Characterization of PET Polymer for Bottle Manufacturing," Presentation given at the Society of Plastics Engineers, Benelux Seminar, May 20-21, 1980.

European Patent Office, Written Opinion in International Application No. PCT/EP2014/051896 (dated Jul. 2, 2014).

International Bureau of WIPO, International Preliminary Report on Patentability in International Application No. PCT/EP2014/051896 (dated Aug. 11, 2015).

State Intellectual Property Office of the People's Republic of China, Notification of the Second Office Action in Chinese Patent Application No. 201480007800.4 (dated Dec. 9, 2016).

Eurasian Patent Organization, Notification on Necessity of Presenting Additional Materials in Eurasian Patent Application No. 201591046/28 (dated Nov. 1, 2016).

Eurasian Patent Organization, Notification on Necessity of Presenting Additional Materials in Eurasian Patent Application No. 201591046/28 (dated Feb. 14, 2017).

Taiwan Intellectual Property Office, Examination Report in Taiwan Patent Application No. 103103368 (dated Apr. 5, 2017).

King Abdulaziz City for Science & Technology, Substantial Examination Report in Saudi Arabian Patent Application No. 515360929 (dated Mar. 26, 2017).

\* cited by examiner

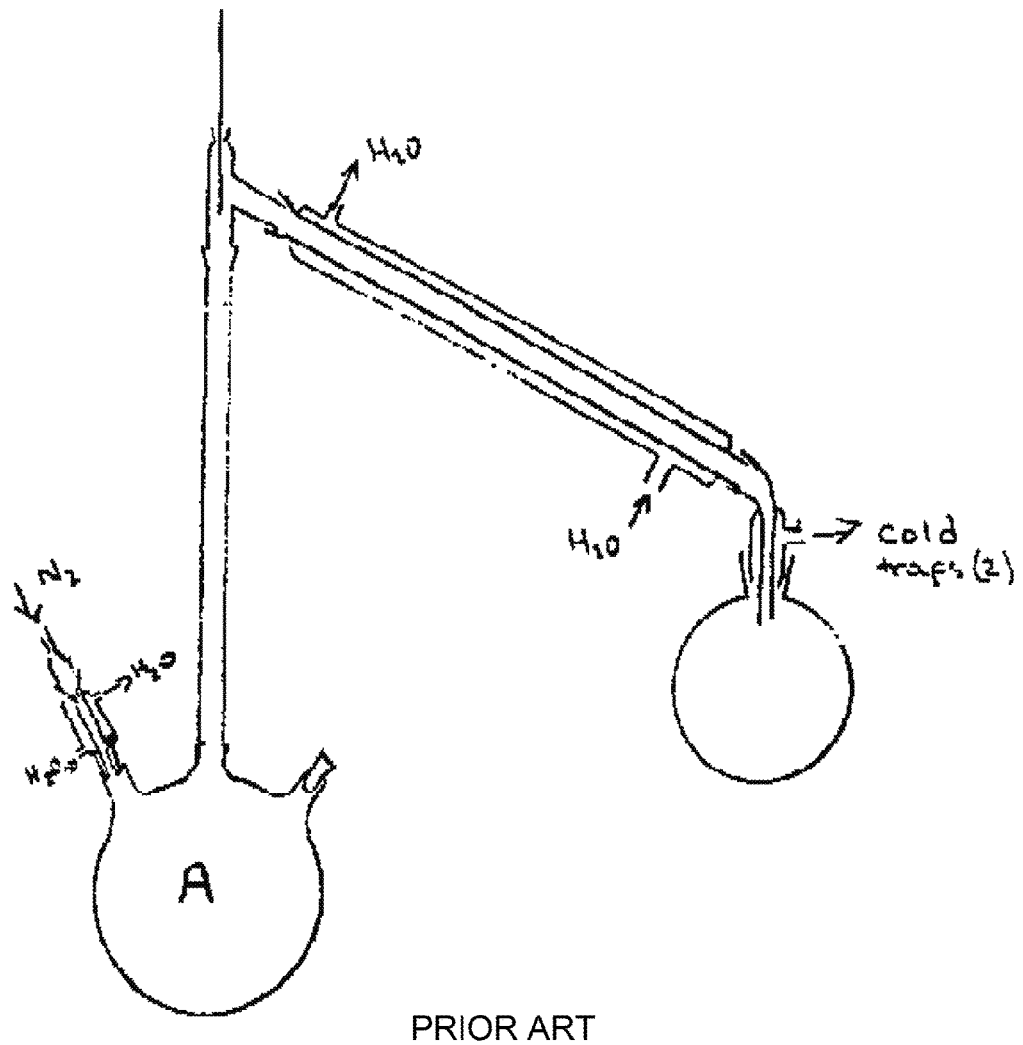
PRIOR ART

METHOD FOR THE PRODUCTION OF A TITANIUM CONTAINING CATALYST, TITANIUM CONTAINING CATALYST, METHOD FOR THE PRODUCTION OF POLYESTER AND POLYESTER

CROSS-REFERENCE TO RELATED APPLICATIONS

This patent application is the U.S. national phase of International Application No. PCT/EP2014/051896, filed on Jan. 31, 2014, which claims the benefit of European Patent Application No. 13154209.4, filed on Feb. 06, 2013, the disclosures of which are incorporated herein by reference in their entireties for all purposes.

Present invention is directed to a method for the production of a titanium containing catalyst, wherein a titanium-(IV)-alkoxide of high purity is reacted with an alpha-hydroxy carboxylic acid. Furthermore the invention concerns a titanium containing catalyst allowing for the production of high viscosity polyesters with high thermal stability. In addition, the invention is directed to a method for the production of polyesters and polyesters themselves.

The thermal stability of polyesters is particularly necessary for extrusion of polyester granulate for e.g. fibre, film and injection moulding applications. The required extrusion temperature in combination with the necessary hold-up time always leads to a certain degree of degradation to the used polyesters. The rate of thermal degradation of polyesters is mainly a function of viscosity, temperature and catalyst type. The rate of degradation is also accelerated in the presence of oxygen. The thermal degradation rate increases with higher polyester viscosity and/or temperature. Thermal degradation causes a quality-wise undesirable rate of (a) loss in viscosity, (b) increased end groups, (c) increase of generated volatile products and/or (d) change in colours (especially higher b* values), and therefore always deteriorate the polyester quality to a certain degree.

For the production of polyesters, catalysts, mostly metal based, are necessary to reduce the reaction time to a commercially affordable period. Catalysts influence not only the main reaction kinetics but also the quality of the final polyester product. Catalysts enhance forward (polymerisation) as well as backward (depolymerisation) reactions and additional undesired side-reactions in terms of polychrome linkage formation. Backward and side reactions count to thermal degradation processes. Different catalysts have different behaviours according to the mechanisms of how they influence the thermal degradation. Catalysts like zinc (Zn), cobalt (Co), and nickel (Ni) are known to be very active in accelerating backward and side reactions but antimony (Sb), germanium (Ge) or titanium (Ti) also show these reactions. Since the early days of polyester invention nearly all elements of the periodic table and combinations of the elements as different compounds were investigated to improve the polymerisation rate and selectivity for optimised quality of polyesters.

To reduce the undesired reactions of the catalyst, very often a phosphorous compound is added to deactivate the metal catalyst. The metal catalyst needs to be in a solvable form to react best and most metals or metal compounds form an insoluble and catalytic inactive precipitation with phosphorous compounds at the polyester processing temperatures. These precipitations lead to undesired haziness in amorphous end products like film and bottles. Excessive amounts of a phosphorous compound may hinder the catalytic activity of the catalyst entirely.

In 1937, the production of polyesters was patented by Wallace H. Carothers. Polyesters, based on TPA, were patented in 1949 by Whinfield and Dickson. At this time polyesters were produced only in batch processes. The introduction of continuous processes in 1960 allowed for large scale production.

All continuous polyester processes consist of the reaction steps 'esterification' and 'polymerisation'. During the esterification TPA and EG react to a diester, called bishydroxy-ethyleneterepthalate (BHET) or monomer. This reaction is autocatalysed by existing $H^+$ ions of the reactants and therefore needs no further externally supplied catalysts.

In the subsequent polycondensation (also called polymerisation) reaction primarily the existing carboxyl and hydroxyl end groups react to long molecular chains while releasing EG. The rate of polycondensation is dependent upon process temperature, residence time, pressure in the vacuum region, surface renewal rates, but catalysts also have a decisive effect on the reaction rate. In 1949, Whinfield and Dickson produced a higher molecular weight PET after 72 hours residence time even without addition of a catalyst. Soon it was recognised that catalysts, for example on the basis of antimony, titanium, aluminium, magnesium, germanium and others can reduce the residence time to a few hours.

Ludewig reported in the Book of Polyester Fibers, Chemistry and Technology, 1975, many previously known catalysts for the polymerisation. He reported the prevailing knowledge of various catalysts, usually metal acetate salts, by order of reactivity. So-called primary catalysts such as antimony, germanium and titanium compounds have the best catalytic quality. So-called secondary catalysts for the polymerisation reaction are based on elements of the $1^{st}$ and $2^{nd}$ periodic table groups, aluminium and manganese. It is well known that the catalysts used have an undesirable impact on viscosity increase or even final viscosity due to back reactions.

In addition to the activity of a catalyst the selectivity in terms of side reactions is important. In PET production side reactions produce mainly yellow discoloration and an undesirable increase in acetaldehyde. Germanium and antimony have the best performance regarding selectivity for PET resulting in many decades of use in commercial production plants, with producers disregarding more reactive titanium compounds due to incompensable formation of polychrome linkages (especially yellowness). For the production of other polyesters like polybutyleneterephthalate or other copolyesters, titanium compounds are preferred as catalysts where yellowing only occurs to a minor extent.

Another important aspect in the use of catalysts is their deactivation in whole or in part, because catalysts also catalyse depolymerisation reactions at different rates. These depolymerisation reactions are noticeable during melt processing, in the SSP step, during extrusion steps or even in the final product. A wide range of phosphorus based deactivation agents, more commonly referred to as stabilisers, are often used to control depolymerisation.

Typically large continuous processes for producing PET divide the polycondensation to high molecular weight PET into two steps; a melt polymerisation and SSP. In the first step PET is polymerised in melt phase to a medium molecular weight up to approximately 18,000 g/mol, corresponding to approximately 100 monomer units and an intrinsic viscosity of about 0.60 dl/g.

This is maybe followed by a direct melt processing into films or fibres or feeding into a granulation system with cooling and cutting of the polymer to obtain defined small PET granulate, often called pellets or chips. These granulates are then fed to a SSP reactor to achieve the final desired high viscosity, high molecular weight polymer. The final molecular weight is determined by the selected process temperature, usually 200-225° C. and the hold-up time. In order to ensure the PET chips suffer no oxidative damage, a carrier gas like nitrogen is used for heat supply and to remove the formed volatile reaction products. The final molecular weight is defined by the desired end-use. PET for manufacturing PET bottles has a molecular weight of approximately 26000 g/mol, which relates to approximately 140 monomer units and an equivalent intrinsic viscosity of about 0.80 dl/g.

Since 2004 a continuous PET process by Uhde Inventa-Fischer, which achieves a molecular weight of about 26000 g/mol directly in the melt with an antimony catalyst system has been known; this eliminates the second SSP step to achieve high viscosity polyesters.

In the last 20 years interest in heavy metal-free catalysts for PET has increased greatly as evidenced by many discussions at worldwide PET congresses and numerous patent applications on this topic. A driving force is not only a higher tolerability for humans and the environment, but also to improve the PET product quality and material processing conditions. In addition to antimony, cobalt and bismuth, used as additives in PET, are also classified as heavy metals.

The patent literature and particularly Ludewig address the replacement of antimony and germanium as polymerisation catalysts by predominantly utilising titanium catalysts in conjunction with co-catalysts and a phosphorous component. Specifically antimony-free or heavy metal free recipes relate to a preparation of medium molecular weight PET melt polymerisation with a maximum intrinsic viscosity of approximately 0.60 dl/g, followed by SSP.

In many patents enormous difficulties have been explicitly mentioned when producing high viscosity polymer melt of approximately 0.80 dl/g, such as yellow discoloration and increased acetaldehyde formation related to the use of antimony-free catalysts.

Jernigan et al. justified in U.S. Pat. No. 7,368,522 [Eastman, Feb. 24, 2006] the inventive step of using antimony to reach an intrinsic viscosity of approximately 0.75 dl/g and acceptable product quality in the melt without further SSP by arguing that the task cannot be fulfilled with titanium catalysts.

Cholod et al. in U.S. Pat. No. 4,356,299 [Rohm and Haas, Feb. 4, 1982] use a hybrid system consisting of an alkyl-titan and antimony compound. It was possible to reach standard intrinsic viscosity of ca. 0.6 dl/g in the melt in less time than usual with antimony while avoiding the disadvantages of a yellow coloration with titanium compounds.

Schaaf et al. in U.S. Pat. No. 6,559,271 B2 [UIF, Sep. 13, 2001] disclose a formulation based on titanium compounds in combination with cobalt, which can be used even up to 280° C. Cobalt acts in this recipe both as co-catalyst as well as blue toner to control the yellow tint. To control the acetaldehyde content the catalysts are deactivated with phosphorous compounds and additionally acetaldehyde binding substances were used. This recipe can be used for higher molecular weights in the melt from 0.63 to 1.00 dl/g intrinsic viscosity.

Moore et al. in U.S. Pat. No. 7,094,863 B2 [Wellman, Nov. 24, 2004] claim an antimony-free catalyst formulation for the production of PET pellets specifically for bottles. Disclosed are improved product properties like dimensional stability and clarity for hot-fill applications. The recipe allows for a cobalt content up to 50 ppm in addition to antimony. The invention relates to polyester production with medium viscosity and the additional use of a SSP.

Yamamoto et al. in U.S. Pat. No. 7,544,762 B2 [Teijin, Jul. 16, 2002] published a heavy metal-free formulation with good colour and low acetaldehyde, based on a titanium-phosphorus component. The viscosity of the melt reached a maximum of 0.64 dl/g.

Fujimori et al. in U.S. Patent 2004/0044173 A1 [Teijin, Aug. 24, 2003] published a heavy metal-free formulation with good colour and low acetaldehyde, based on a titanium-phosphorus component and adding periodic group element compounds Ia, IIa, Mg, Fe or Co. The achieved maximum viscosities of the melt are 0.64 dl/g, therefore, a SSP is needed to achieve higher viscosities.

Siddiqui et al. in patent application WO 2004-065452 A1 [Sabic, Jan. 23, 2003] uses a Ti—Na-glycolate catalyst system and achieved viscosities of 0.63 to 0.66 dl/g in the melt. Here too, a SSP is necessary to increase the molecular weight.

Ohmatsuzawa et al. in patent EP 1013692 [Mitsui, Dec. 23, 1999] uses a solid titanium catalyst, obtained by dehydration of a titanium halide compound and reaction with a P compound and the use of a magnesium compound as a co-catalyst. As an alternative to Mg elements of periodic group IIa and heavy metals are also mentioned. The results obtained in terms of viscosities are approximately 0.65 dl/g and require a SSP to achieve higher viscosities.

Partridge et al. in U.S. patent 2007/010648 A1 [Johnson Matthey, May 10, 2004] use either Ti, Zr and Hf with 2-hydroxy carboxylic acids and a quaternary ammonium compound instead of simple Ti-alkoxides. Even here the viscosities obtained in the melt are only approximately 0.62 dl/g and require a SSP to achieve higher viscosities.

Qi et al. in patent EP 2006 315 [Toray, Dec. 21, 2008] also use a titanium, phosphorus and co-catalyst system for the production of PET, wherein the co-catalyst is preferably a mixture of Mg, Mn, Ca and Co. This system delivers a melt viscosity of approximately 0.67 dl/g.

In patent application WO 2008/150350 A1 [Eastman, May 23, 2007] Jernigan describes a Ti-based catalyst system with a later phosphorous addition to the PET manufacturing process, with which a high viscosity in the melt at a shorter reaction time can be achieved with low acetaldehyde content. The use of a SSP is considered to be no longer necessary. The patent also describes the use of other additives, including the use of titanium nitride (TiN). In contrast to commercial reality, extremely high amounts of toners (red 7-9 ppm, blue 13-18 ppm) are used and the generated colour values are extremely distorted by the toners. The high toner addition level is required to mask the yellow colouration formed during extrusion processing of the PET granulates prior to commercial use.

Schönnagel in US 2012/088898 A1 disclose a catalyst mixture comprising a titanium containing compound, a co-catalyst and a blue toner to achieve a high viscosity polyester melt with very good colours. The patent mentioned also titanium-(IV)-alkoxides but always used in a mixture with other components and not used alone in a high purity. Furthermore the mixture enables the production of polyesters with high viscosity and good colour but not with a high thermal stability. However, it is known from the state of the art, that organic titanium species have a strong tendency to be oxidized to titanium oxide species, which render the catalysts ineffective.

The polymerisation of high viscosity polyesters, especially PET, is done commercially with an antimony catalyst system. Other catalyst systems tend to have higher thermal degradation behaviour which results especially in a loss of viscosity, increase in COOH endgroups and AA increase during re-extrusion. The task of this invention was to demonstrate an alternative catalyst system to antimony with lower thermal degradation behaviour, especially during re-extrusion. To simulate the thermal degradation during re-extrusion a highly persuasive thermal degradation procedure was defined.

Starting from this prior art it is the objective of the present invention, to provide catalysts for the production of polyesters, enabling the production of polyester with high viscosity as well as high thermal stability.

This objective is solved by the method for the production of a titanium containing catalyst described herein, a titanium containing catalyst, a method for the production of a polyester and a polyester with the features described herein. Advantageous embodiments are also described.

According to a first aspect of the invention, a method for the production of a titanium containing catalyst is provided, the method comprising of reacting at least one titanium-(IV)-alkoxide of the general formula Ti(OR)$_4$ wherein—each R is the same or different of a linear or branched alkyl group with 1 to 32 carbon atoms, with at least one alpha-hydroxy carboxylic acid, thereby forming one or more titanium alpha-hydroxy carboxylate species and an alcohol with the formula ROH, wherein—the overall content of the sum of all titanium oxide species, relative to the at least one titanium-(IV)-alkoxide, Ti(OR)$_4$ is ≤10.0 mol.-%.

The crucial point of present invention is the fact that the starting material i.e. the titanium-(IV)-alkoxide, is used in a high purity, namely having a low content of titanium oxide species, which lies below 10.0 mol.-%.

According to present invention, the term "titanium oxide species" understands every titanium compound comprising at least one oxygen atom in form of an oxide. Therefore, this term encompasses species like TiO$_2$, TiO$_x$ and all mixed oxides of titanium, comprising an oxide-oxygen as well as other organic residues. Especially, compounds according to the general formula TiO$_x$(OR)$_{4-2x}$ with 0<x<2 and R as defined above are encompassed by this definition.

Surprisingly it was found, that the product emerging from this reaction, i.e. the titanium containing catalyst enables the production of polyesters with a high thermal stability as well as high viscosity. Evidently the purity of the titanium catalyst, especially as far as its content of titanium oxide species is concerned, has an beneficial effect on the properties of the resulting polyester.

According to a preferred embodiment, the overall content of the sum of all titanium oxide species relative to the at least one titanium-(IV)-alkoxide is ≤4.00 mol.-%, preferably ≤2.00 mol.-%, more preferably ≤1.00 mol.-%, more preferably ≤0.60 mol.-%, more preferably ≤0.30 mol.-%, especially preferred ≤0.01 mol.-%.

Furthermore, it is advantageous that the alpha-hydroxy carboxylic acid is selected from the group consisting of citric acid, lactic acid, tartaric acid and malic acid.

Preferred residues R as defined in the above mentioned general formula are selected from the group consisting of i-propyl, methyl, ethyl, n-propyl, n-butyl, i-butyl, t-butyl, all possible isomers of pentyl, all possible isomers of hexyl, all possible isomers of heptyl, all possible isomers of octyl; wherein i-propyl is especially preferred.

Furthermore, it is advantageous if the molar ratio of the at least one alpha-hydroxy carboxylic acid relative to titanium in the at least one titanium-(IV)-alkoxide in the above mentioned reaction ranges from 1 to 4, preferably 2 to 2.9, especially preferred from 2.4 to 2.6.

The at least one alpha-hydroxy carboxylic acid can be present as solution, preferably an aqueous solution, more preferred an aqueous solution with an overall content of the at least one alpha-hydroxy carboxylic acid from 10 wt.-% to the limit of solubility, especially preferred an aqueous solution with an overall content of the at least one alpha-hydroxy carboxylic acid from 30 wt.-% to 90 wt.-%, and the at least one titanium-(IV)-alkoxide is added to the solution of the at least one alpha-hydroxy carboxylic acid.

In addition, it is possible, that after completion of the reaction at least a part or all of the alcohol with the formula ROH is removed from the reaction mixture, preferably by distillation. However, it is also possible, that the alcohol ROH resulting from the underlying chemical reaction can remain in the titanium containing catalyst.

Further preferred embodiment foresees that after completion of the reaction, water is added, preferably after the removal of the alcohol ROH as described before, until a titanium content, calculated as Ti, from 0.1 wt.-% to 50 wt.-%, preferably 1 wt.-% to 20 wt.-%, especially preferred 2 wt.-% to 7 wt.-% is obtained. The concentration of the catalyst is calculated as Ti alone, i.e. when calculating the concentration, the organic residues such as the alpha-hydroxy carboxylic acid and/or the alcohol are not considered.

Alternatively, it is also possible, that after completion of the reaction all solvents are removed and the one or more titanium alpha-hydroxy carboxylate species is/are obtained as neat or solid substance.

According to a second embodiment of present invention a titanium containing catalyst is provided, which preferably comprises one or more titanium alpha-hydroxy carboxylate species, which has an overall content of the sum of all titanium oxide species relative to the sum of all titanium alpha-hydroxy carboxylate species of ≤10.00 mol.-%, preferably ≤4.00 mol.-%, more preferably ≤2.00 mol.-%, more preferably ≤1.00 mol.-%, more preferably ≤0.60 mol.-%, more preferably ≤0.30 mol.-%, especially preferred ≤0.01 mol.-%.

In a special embodiment, the titanium containing catalyst according to the invention can be produced with an inventive method as described above.

According to the invention, the purity of the used starting materials used for producing the titanium containing catalyst also has an impact on the resulting purity of the titanium containing catalyst itself as far as the oxide content is concerned.

The low titanium oxide species content characteristic of the titanium catalyst is preserved and also protected from formation of titanium oxide species during product storage and use, by stabilising chelating ligands, such as the alpha-hydroxy carboxylic acids described.

Without being bound by theory, other stabilising chelating ligands could be expected to perform the same role of the alpha-hydroxy carboxylic acid, in preserving and also protecting the titanium catalyst from formation of undesirable titanium oxide species during product storage and use.

It is possible that the titanium containing catalyst is present as solution, preferably an aqueous solution with a preferred pH value in the range of 0 to 4, preferably 1 to 4 or a solution in an alkane diol selected from ethylene glycol, 1,3-propyeneglycol, 1,4-butanediol or mixtures thereof, with a preferred titanium content, calculated as Ti, from 0.00001 to 99.999 wt.-%, preferably from 0.1 wt.-% to 50 wt.-%, more preferably ≤1 wt.-% to 20 wt.-%, especially preferred 2 wt.-% to 7 wt.-%.

Alternatively, the titanium containing catalyst can also be present as neat or solid substance.

The titanium containing catalyst can comprise one or more additional components, such as e.g. at least one of a co-catalyst, a toner, an inhibitor, a phosphorous compound, a scavanger, a crosslinker, an endgroup modifier, a dulling agent, a reheat additive or mixtures of two or more of the same or different aforementioned compounds.

A further aspect of present invention is directed to a method for the production of a polyester, which can be conducted by either polycondensation of at least one dicarboxylic acid with at least one dialcohol, or transesterification of at least one diester of at least one dicarboxylic acid with at least one dialcohol. The inventive method for the production of a polyester uses a titanium containing catalyst, as described before. This titanium containing catalyst is added before, during and/or after the polycondensation reaction or transesterification reaction, i.e. added to the starting materials, during the respective reaction of the starting materials and/or after completion of the respective reaction.

Preferably, the titanium containing catalyst is added to the polycondensation reaction or transesterification reaction, respectively, in an amount resulting in a titanium content, calculated as Ti, from 1 to 1000 ppm, preferably from 2 to 500 ppm, especially preferred from 3 to 25 ppm in the resulting polyester.

In a preferred embodiment, after the polycondensation or transesterification, respectively, the obtained polyester is postcondensated and/or subjected to a reduction of contained volatiles, especially acetaldehyde.

The method for the production of a polyester can be carried out in a batch wise or continuous process.

Especially preferred is a reaction for the production of polyethylene terephthalate (PET), which can be accomplished by either polycondensation of terephthalic acid with ethylene glycol or by transesterification of bishydroxy ethylene terephthalate (BHET) with ethylene glycol.

PET belongs to the group of polyesters, which are characterised by the reaction of a dicarboxylic acid or esters thereof with a diol to build up long-chain molecules. In PET, the dicarboxylic acid is terephthalic acid, hereinafter referred to as TPA and the diol is ethylene glycol, hereafter referred to as EG. Also other dicarboxylic acids like isophthalic acid and/or other diols like diethylene glycol are sometime incorporated to a certain extent to modify the polyester properties. At present, the global PET production is about 36 million tons per year and has particular applications in the production of bottles, packaging, fibres and engineering polymers.

Most PET is produced in two continuous steps. The first step is the production of a medium viscosity PET in the liquid or melt phase with subsequent formation of granulate (also chips, pellets) by cooling and cutting. The second step is a viscosity increase of the PET in a solid state postcondensation reactor, hereafter referred to as SSP.

For the polymerisation of high viscosity polyester, in particular for the polymerisation of PET a high purity titanium catalyst has been used. Surprisingly it was found that PET polyester produced with this catalyst shows a significantly improved thermal stability. The thermal degradation rate of this polyester was better than the reference with standard antimony catalyst type or alternative titanium catalysts in terms of lower loss of viscosity, lower increase in COOH end groups, lower increase of generated volatile products like AA and lower change in colours.

Yet another aspect of present invention concerns a polyester, which contains a catalyst as described before and/or is producible according to a method as described before.

In a preferred embodiment, this polyester is polyethylene terephthalate (PET).

Preferred characteristics of this polyester are:
a) an intrinsic viscosity (IV) of more than 0.70 dl/g,
b) an increase of the concentration of COOH-endgroups, measured at 290° C., of ≤2 mmol/kg within 10 min,
c) an increase of acetaldehyde formation, measured at 290° C., ≤1 ppm per min
d) a decrease of the L*-colour, measured at 290° C., ≤1 unit per min and/or
e) an increase of the b*-colour, measured at 290° C., ≤0.4 units per min.

Present invention is described in greater detail with reference to the following examples and specifications. However, the scope of the invention is not restricted to the special embodiments as described in the following.

1. Method for the Production of the High Purity Titanium Catalyst 1.1 Starting Materials Sample 1

Tetra-isopropyl orthotitanate, VERTEC® TIPT, 97+ w/w % purity was used as supplied by Alfa Aesar.

Sample 2

Tetra-isopropyl orthotitanate, VERTEC® TIPT, 97+ w/w % purity was vacuum distilled using a 15 cm unpacked column (50 mbar, 134° C.) to provide a clear, colourless liquid.

Sample 3

Tetra-isopropyl orthotitanate, IG Ultra-Pure TIPT, 99.8+ w/w % purity, 99.99999 w/w % metals purity, was used as supplied by Catalytic Technologies Ltd.

TIPT Characterisation

TABLE 1

| TIPT Sample | Ti Assay (w/w %)* | Total Volatiles (w/w %)** | Corrected Ti Assay (w/w %)*** | Corrected Ti assay differential from 100% pure theoretical (w/w %)**** | Corrected Ti assay differential from theoretical (%)***** |
|---|---|---|---|---|---|
| 1 | 17.15 | 0.3 | 17.20 | 0.36 | 2.14 |
| 2 | 17.02 | 0.1 | 17.04 | 0.20 | 1.19 |
| 3 | 16.88 | 0.0 | 16.88 | 0.04 | 0.24 |

*Ti assay calculated using analysis method 1.
**Total volatiles calculated using analysis method 2.
***Corrected Ti assay calculated using [(100 × (Ti Assay))/(100 − (Total Volatiles))].
****Corrected Ti assay differential from 100% pure theoretical calculated using [(Corrected Ti Assay) − 16.84].
*****Corrected Ti assay differential from theoretical calculated [(Corrected Ti assay differential from theoretical)/16.84) × 100].

1.2. General Method for the Production of a High Purity Titanium Catalyst (Titanium Citrate Preparation)

TIPT samples 1, 2 and 3 (284 g, 1.0 mol) were independently charged to a flask containing 50 w/w % aqueous citric acid solution (963 g, 2.5 mol). The 2-propanol was removed from the solution via distillation. The titanium citrate solution was diluted with distilled water to 5.0 w/w % Ti and used for polyester synthesis without further processing. TIPT sample 1 provided titanium citrate sample 1; TIPT sample 2 provided titanium citrate sample 2; TIPT sample 3 provided titanium citrate sample 3.

1.2 Analysis Methods.

Method 1 Titanium Assay Determination Using a Metrohm Auto-Titrator

Outline

The titanium content of a sample is determined by digestion with hydrochloric acid, reduction using chromous chloride followed by titration with standardised ferric ammonium sulphate (ferric alum) solution using an autotitrator.

Apparatus

Analytical Balance (capable of weighing to 0.1 mg)
721 NET TitrinoMetrohm Auto-titrator system including PC and software
775 DosimatExMetrohm
Magnetic stirrer and follower
Hotplate with magnetic stirrer, follower, water bath and temperature controller
Hotplate
1 L volumetric flasks
Beakers (400 ml and 150 ml tall form)
Watch glasses
Measuring cylinders (25 ml and 500 ml)

Materials

Conc. hydrochloric acid GPR Grade
Conc. sulphuric acid GPR Grade
Ammonium ferric sulphate dodecahydrate GPR Grade
Ammonium sulphate GPR Grade
Mercury GPR Grade
Zinc dust GPR Grade
Chromium (III) potassium sulphate dodecahydrate GPR Grade
Potassium chloride GPR Grade
Potassium permanganate 0.02 mol (0.1 N) convols (to 1 L) Ex BDH (or similar)
Titanium (IV) oxide 99.9%+(Ex Aldrich or similar)
De-ionised water
Nitrogen (for sparging) HP Grade
Anti-bumping granules Procedure Potassium Permanganate Solution:

Position an ampoule of 0.02 mol potassium permanganate inside the neck of a 1 L volumetric flask, using a piece of glass rod break the top membrane. Push the rod through the ampoule and break the lower seal. Partially withdraw the glass rod and allow the solution to drain into the volumetric flask, rinse the glass rod and ampoule into the volumetric flask with de-ionised water and then dilute to volume with de-ionised water.

Ammonium Ferric Sulphate (Ferric Alum) Solution (N/16):

Weigh 30 g of ferric alum into a 1 L volumetric flask and dissolve in approximately 300 ml of de-ionised water. Carefully add 10 to 12 ml of conc. sulphuric acid and mix thoroughly. Dilute to within approximately 5 ml of the mark and add dropwise the potassium permanganate solution to give a faint pink colouration. Dilute to volume with de-ionised water and mix. The solution must be allowed to stand for a minimum of 48 hours, and be factorised prior to use.

Zinc/Mercury Amalgam:

Into the 500 ml Schott bottle (supplied with the autotitrator system) add approximately 250 g of mercury and 9 g of zinc dust (granules may be used, but are slower). Place on the magnetic stirrer, add the follower and stir for approximately 24 hours.

Chromous Chloride Solution (10% in 10% HCl):

Into a suitable beaker weigh 100 g of chromium (III) potassium sulphate dodecahydrate, add approximately 100 ml of de-ionised water and 10 ml of conc. hydrochloric acid and dissolve. Transfer the solution to a 1 L volumetric flask rinsing the beaker with de-ionised water. Add approximately 700 ml of de-ionised water and 90 ml of conc. hydrochloric acid, mix well and dilute to volume with de-ionised water. Transfer a portion of this solution into the 500 ml Shott bottle containing the prepared zinc/mercury amalgam, fit the nitrogen sparge, trap and transfer line from the Dosimat 775. Start the nitrogen sparge and continue stirring. The colour will change from a green/blue to a sky blue when ready for use. Periodically the colour may revert to a green/blue, if this happens check the nitrogen sparge is satisfactory, if still green/blue try addition of zinc dust, if still green/blue discard solution, rinse the amalgam with water and top up with fresh chromous chloride solution.

Factorisation of the Ferric Alum Solution:

Into a 150 ml beaker weigh 0.15 to 0.25 g of titanium (IV) oxide record the weight to 4 decimal places. Add 15 ml (or 27.6 g) of conc. sulphuric acid and 10 g of ammonium sulphate. Cover with a watch glass and heat to dissolve the titanium oxide (hotplate set to 400° C.). When the titanium oxide appears to have dissolved maintain the heat for a further 5 minutes. Remove from the hotplate and cool to ambient temperature prior to titrating. Quantitatively transfer the contents of the beaker to the titration cup and make up to the mark with de-ionised water. Add the follower, fit the lid on the cup, insert the electrodes, the nitrogen purge and the 721 NET and 775 Dosimat outlets to the lid and place the cup in a water bath on the hotplate. Turn on the nitrogen purge to the cup, the heater and the stirrer and allow the cup to reach a temperature of approximately 70° C. Follow standard procedures until standardisation is complete.

Titanium Content:

Weigh the appropriate amount of sample into a 150 ml beaker and record the weight to 4 decimal places, add a few anti-bumping granules, 30 ml of conc. hydrochloric acid and 30 ml of de-ionised water. Cover the beaker with a watch glass and heat on a hotplate to digest for at least 20 min. When fully digested remove from the hot plate and allow to cool. Quantitatively transfer the contents of the beaker to the titration cup and make up to the mark with de-ionised water. Add the follower, fit the lid on the cup, insert the electrodes, the nitrogen purge and the 721 NET and 775 Dosimat outlets to the lid and place the cup in the water bath on the hotplate. Turn on the nitrogen purge to the cup, turn on the heat and stirrer and allow the cup to reach a temperature of approximately 70° C. Complete the titration using the autotitrator as per the manufacturer's instructions.

Calculations

Ferric alum factorisation $(N)$=Weight of titanium oxide$\times 0.999 \times 1000\{$(End point 2–End point 1)$\times 79.9\}$.

Titanium content (%)=(End point 2–End point 1)$\times 0.001 \times N \times 47.9 \times 100$ Weight of sample.

Method 2—Determination of Volatiles in TIPT
Suggested Apparatus
GC system with data processing
50 m WCOT Fused Silica Capillary Column (0.53 mm ID, DF=5.0), coating
CP-SIL5CB
Fused silica capillary column
5 μl syringe
2×100 ml 3-necked flask
500 ml flask (receiver)
2 condensers
Distillation head
30 cm unpacked distillation column
Receiver adaptor
Isomantle (1000 ml) with controller
Clamp stand, boss and clamp
Thermometer: −20 to 110° C. with B19 adaptor (BS 1704, Ref B60/100)
Balance (4 decimal places)
0-2 L/min nitrogen rotameter
Reagents
Anti-bumping granules
GPR cyclohexane
Analar n-propanol
Analar iso-propanol
Analar heptane
Distillation Place some anti-bumping granules in flask A and fit the stoppers. Weigh this apparatus empty [W1]. Pour in approximately 170 g of sample and reweigh [W2]. Add 350 ml of cyclohexane and reweigh [W3]. Weigh the empty receiver flask [W4]. Set up the apparatus as in FIG. 1. Ensure that the water is flowing through the condensers and that nitrogen is flowing through the rotameter at 0.5 L/min. Set the isomantle controller to 60% and apply heating. Heat to boiling and collect approximately 300 ml of distillate. Throughout the distillation maintain the nitrogen flow at 0.5 L/min. Weigh the receiver flask and distillate [W5]. Weigh flask A [W6].

Preparation of Calibration Solution

Into a clean, dry 10 ml volumetric flask accurately weigh approximately 0.3 g of n-propanol [W7], 0.3 g of iso-propanol [W8] and 0.3 g heptane [W10]. Dilute to volume with cyclohexane.

Preparation of Sample Solution

Into a clean dry 100 ml volumetric flask accurately weigh approximately 0.3 g of n-propanol [W9]. Dilute to the mark with the distillate collected and shake well.

Analysis

Set up the gas chromatograph using the appropriate conditions.

1. Calibration

Inject 1 μl aliquots of the calibration solution. Calculate the response factor (Rf) for iso-propanol using the following equation:

$$Rf_1 = \frac{\text{Area of n-propanol peak} \times W8}{\text{Area of iso-propanol peak} \times W7}$$

Calculate the response factor (Rf) for heptane using the following equation:

$$Rf_2 = \frac{\text{Area of n-propanol peak} \times W10}{\text{Area of heptane peak} \times W7}$$

Agreement in Rf of 0.01 for two consecutive injections is required.

2. Sample Analysis

Inject 1 μl aliquots of the sample solution.

Calculate the % free iso-propanol using the following equation:

$$\% \text{ Free iso-propanol} = \frac{Rf1 \times \text{Area of iso-propanol peak} \times W9X(W5-W4)}{\text{Area of n-propanol peak} \times (W2-W1) \times 0.778}$$

Calculate the % heptane using the following equation:

$$\% \text{ heptane} = \frac{Rf2 \times \text{Area of heptane peak} \times W9X(W5-W4)}{\text{Area of n-propanol peak} \times (W2-W1) \times 0.778}$$

3. Mass balance

The % distillate lost can be calculated from the following equation:

$$\% \text{ loss} = \frac{(W5-W4)}{(W3-W6)} \times 100$$

W1 to W9 correspond to the weights used at each stage in the analysis process as described above and should be recorded for each sample analysed.

2. Method of Production of Polyester Using the High Purity Titanium Catalyst 2.1. General Method for Production of a Polyester The Ti catalyst can be used for the production of any polyester which is characterised by the reaction of a dicarboxylic acid or esters thereof with a diol to build up long-chain molecules. The Ti catalyst can also be used if more than one dicarboxylic acid and more than one diol are incorporated to a certain extent to modify the polyester properties. The dicarboxylic acids and diols may be based on renewable sources.

The Ti catalyst can be used as neat substance, or as a solution or dispersion in any carrier substance. The Ti catalyst can also be modified with other ligands in addition to alpha-hydroxy carboxylic acids or modified with other ligands instead of alpha-hydroxy carboxylic acids. Preferably the ligands protect the low levels of titanium oxide species characteristic of the titanium catalyst. Most preferred is the titanium citrate as a solution in ethyleneglycol or butanediol between 0.00001 and 99.999 w/w %.

The Ti catalyst can be mixed with other substances like co-catalysts, toners, inhibitors, phosphorous compounds or other additives before, during or after adding to the polyester process. The addition of the Ti catalyst can be split into several streams and each of these streams can be added at different stages into the polyester process.

The Ti catalyst can be added in amounts of 1 to 1000 ppm titanium into the final polyester polymer, more preferred in amounts of 2 to 500 ppm titanium in the final polyester polymer, for PET polyesters most preferred in amounts of 3 to 25 ppm titanium in the final polymer. There is also the possibility to combine the Ti catalyst with the standard antimony catalyst types or other co-catalysts in any concentration. It is possible to reduce the standard amount of antimony used to produce PET to one third, half or to a minimum.

The Ti catalyst can be added alone or together with one or more raw materials at the beginning of the polyester process or at any time into any stage of the polyester process. Preferred addition is before or after the esterification process of the dicarboxylic acid and the diol. The esterification process can proceed up to a conversion rate of 99.9%, measured according to the release of water during the esterification process. The temperatures during esterification can be 150 to 300° C. at a pressure of 0.03 to 3 MPa.

To reduce undesired reactions of the catalysts included in the raw materials and other additives, a phosphorous compound can be added up to an amount where the catalytic activity of the Ti catalyst is not hindered. The use of the Ti catalyst is also possible without the use of any phosphorous compounds. The phosphorous compound can be any special compound or a commercially available phosphorous compound such as phosphoric acid or triethylphosphate. The addition of the phosphorous compound can be pure or diluted in any carrier substance. The phosphorous compound can be added pure or mixed with other substances like the Ti catalyst, co-catalysts, toners, inhibitors, or other additives before or during or after adding to the polyester process. The phosphorous compound can be added alone or together with one or more raw materials at the beginning of the polyester process or at any time into any stage of the polyester process. Preferred addition is before or after the esterification process of the dicarboxylic acid and the diol. The phosphorus compound can be added in amounts of 0 to 500 ppm phosphorus in the final polyester polymer, more preferred in amounts of 5 to 100 ppm phosphorus in the final polyester polymer. For PET polyester most preferred in amounts of 5 to 35 ppm phosphorus in the final polymer.

Depending on the end-use of the produced polyester there is no restriction to add other additives to achieve certain product properties together with the use of the Ti catalyst. For example there is no restriction to add simultaneously $TiO_2$ for gaining a dulling effect, to add any toners to improve colour values, to add reheat additives like TiN or carbon black powder to improve reheat properties or influence colours, to add magnesium salts to improve pinning properties for film or to add other co-catalysts to improve the catalytic activity. With the use of the Ti catalyst there is no need to add additional acetaldehyde scavenger, however, acetaldehyde scavengers could be added.

The Ti catalyst can also be used to produce slow crystallising PET polyesters with low crystallisation degree. The marginal amount of catalyst used, approximately 10 ppm Ti, generates very few crystal nuclei in comparison to commercially used 250 ppm antimony for PET. The effects of slow crystallising polyesters will be lower energy demand for re-melting, a higher clarity and lower shrinkage properties.

2.2. Result and Discussion

Those having ordinary skill in the art understand that catalysts are necessary to reduce the reaction time to a commercially affordable polyester process and that they influence not only the reaction kinetics but also the quality of the final polyester product. Catalysts enhance forward as well as backward reactions and additional undesired side-reactions. These backward and side reactions count to thermal degradation processes. The higher the desired viscosity, which is equivalent to the length of the polyester chain, the more difficult it is to achieve good polymer properties. State of the art titanium catalysed, high viscosity polyesters are known to be less thermally stable and tend to generate yellow to brown polychromes at usual reaction temperatures.

Thermal degradation occurs during the melt phase reaction as well as during re-melt processes. Re-melt processes are used when polyester granulate is re-melted for example via extrusion processes to form fibres, film, preforms or other containers. The thermal degradation causes a quality-wise undesirable rate of (a) loss in viscosity, (b) increase of end groups, (c) generation of volatile products and/or (d) change in colours (higher b* values), and therefore always deteriorate the polyester quality to a certain degree.

It is known from "Thermal degradation of PET—A kinetic analysis of gravimetric data", Covney, J. D., Day, M. and Wiles, D. M., J. Appl. Polym. Sci., 28, 2887 (1983), that thermal degradation of PET increases with higher viscosity, longer reaction times and at higher temperature. To determine the degradation rates an exact procedure is of high importance.

It is important to control the generation of acetaldehyde (AA) as a thermal decomposition product in the PET bottle processing during the melt phase process as well as during the re-melting process. From Wick, G., "Characterization of PET Polymer for Bottle Manufacturing", presentation given at the Society of Plastics Engineers, Benelux Seminar, May 20-21, 1980, Amsterdam and published in "Modern Polyesters", John Scheirs and Timothy E. Long, Wiley 2003, page 486, it is known that the AA regeneration rate of PET at 290° C. in air could be up to 130 ppm after 10 min.

From "Polyesterfasern", Dr. Hermann Ludewig, Akademie-Verlag Berlin, 1975, page 132-139, it is known that temperature has the major influence on thermal degradation but following second order kinetics and is dependent on the amount of catalyst used. In any case thermal degradation causes a loss in viscosity by chain scission, thus resulting in increased COOH end groups.

Introducing high purity Ti catalyst it was surprisingly found that the overall thermal degradation was remarkably reduced for high viscosity PET polyester in comparison with the standard antimony catalyst system or in comparison with other commercially available titanium catalysts.

In the investigation a batch reactor was used, a continuous process and also an extrusion process. For an accurate comparison all process conditions and amount and type of the phosphorous component were kept constant and only the catalyst type was varied between;

1. a standard antimony glycolate catalyst (Antraco, Youngsun® Antimony Glycolate),
2. a standard Ti catalyst (VERTEC®TIPT, 97+ w/w % purity, as citrate)
3. and the claimed Ti catalyst (Catalytic Technologies Ltd., IG Ultra-Pure TIPT, 99.8+ w/w % purity, as citrate).

The degradation rate testing was carried out as described at 290° C. for 10 minutes, under a nitrogen atmosphere, utilising a heated salt bath.

The results from the batch experiments (examples A, B and C) showed an equivalent reactivity in the melt phase of high purity Ti citrate catalyst 3 and the standard antimony catalyst, but surprisingly during the degradation test the viscosity loss was significantly lower with approximately 0.02 dl/g/min for high purity Ti citrate catalyst 3 and approximately 0.03 dl/g/min for the antimony catalyst. After two hours reaction the standard Ti citrate catalyst 2 showed a decreasing viscosity which indicates that even in the melt phase the polymer chain scission reaction was stronger than the chain growth reaction and therefore the thermal degradation rate was higher. The lower degradation rate of approximately 0.013 dl/g/min for the standard Ti citrate catalyst 1 is attributed to the lower achieved viscosity of 0.71 dl/g versus 0.78 dl/g achieved with standard antimony and high purity Ti citrate catalyst 3.

Furthermore the results from the batch experiments showed a slight decrease in COOH end group generation during the degradation test of 2.2 mmol/kg/min with the high purity Ti citrate catalyst 3 in comparison with the standard antimony catalyst with 2.3 mmol/kg/min and 3.6 mmol/kg/min with the standard Ti citrate catalyst 2. After the melt phase reaction the lowest COOH endgroup concentration was obtained with the high purity Ti citrate catalyst 3.

The results from the batch experiment also showed an unexpectedly high decrease of acetaldehyde generation during the degradation test of 0.3 ppm/min with high purity Ti citrate catalyst 3 in comparison with the standard antimony catalyst with 1.9 ppm/min and 3.7 ppm/min with the standard Ti citrate catalyst 2. After the melt phase reaction the lowest acetaldehyde concentration was reached with high purity Ti citrate catalyst 3 and even after the degradation test gave only approximately 20 ppm which is much lower than known from the state of the art.

The results from the batch experiment further showed unforeseen results with respect to the thermal degradation impact on the polymer colours. The best b* colour was achieved with the standard antimony catalyst 1 but during the degradation test high purity Ti citrate catalyst 3 showed a lower increase in b* colour of 0.2 units/min than the standard antimony catalyst with an increase of 0.3 units/min. High purity Ti citrate catalyst 3 performed better than standard Ti citrate catalyst 2 during the melt phase reaction regarding achieved b* colour. During the degradation test the change in a* colour was equivalent for the standard antimony and high purity Ti citrate catalyst 3 with −0.1 units/min. During the degradation test the loss in L* colour was lower for the standard antimony catalyst with −0.1 units/min than for high purity Ti citrate catalyst 3 with −0.3 units/min, however achieved L* colour with high purity Ti citrate catalyst 3 was better after the melt phase reaction as well as after the degradation test. High purity Ti citrate catalyst 3 performed much better during the degradation test than the standard Ti citrate catalyst 1 which lost 0.6 units/min L* colour.

The continuous pilot line experiment was only carried out with a standard antimony catalyst 1 and high purity Ti citrate catalyst 3. The continuous pilot line was designed to mimic a standard commercial line to produce polyesters from dicarboxylic acids and diols and the results are more comparable to expected commercial results than batch reactor experimental results. The amount of catalysts used and dosing places for the catalyst and the phosphorous compound were chosen for gaining best results in a first attempt but may be varied as described previously. The raw material ratios and process conditions were chosen for the production of PET polyester with a certain throughput and can be varied for other throughputs or for other polyesters.

The degradation results from the continuous experiments (example D and E) demonstrated that under the same process conditions and equivalent high melt viscosity of about 0.88 dig for the standard antimony catalyst and 0.83 dl/g for high purity Ti citrate catalyst 3, high purity Ti citrate catalyst 3 showed a slightly lower IV loss, a significantly lower increase in COOH endgroups and AA formation and a lower loss of L* and lower increase of b* colour values. These results confirm the lower thermal degradation behaviour for high purity Ti citrate catalyst 3 of the previous batch experiments.

After a 12 hour heat treatment of the PET polyester granulates made by the continuous process with a temperature profile from 120 to 180° C. under atmospheric pressure air flush to reduce the acetaldehyde content below 1 ppm, the granulates were converted via re-extrusion and injection moulding processes into preforms, the precursors for a bottle. The re-extrusion process re-melts the granulates with a temperature profile of 270 to 300° C. within 4 min and the degradation procedure is simulating that process.

The results of the difference before the re-extrusion process and after the re-extrusion process show clearly that the preform based on the high purity Ti citrate catalyst 3 shows lower thermal degradation related to a lower loss of viscosity, a lower increase in COOH endgroups and a lower increase in AA content compared to the preforms based on a standard antimony catalyst 1. Also the colour of the preform based on titanium catalyst 3 was good, with comparable b*-colour values to the standard antimony catalysis.

2.3. Batch Reactor Experiments

EXAMPLE A

Example A is the standard antimony reference performance in a batch reactor. The standard antimony was Youngsun® Antimony Glycolate from Antraco. Final content of antimony (Sb) was calculated with 270 ppm and phosphorus (P) was calculated with 20 ppm in the finished polymer. The ratio of BHET to final polymer was calculated with 210/192.

A polyester polycondensation reaction is performed in a 60 ml glass flask reactor which is equipped additionally with a glass stirrer, a side glass tube for taking samples, a 50 ml glass flask connected to the top of the 60 ml glass flask to collect the off diol, a connection to purge nitrogen and a connection to vacuum.

50 g of bis-2-hydroxy-ethylene-terephthalate (BHET), the esterification product from the reaction of the dicarboxylic acid terephthalic acid and the diol monoethyleneglycol, was ground to approximately 3 mm size and was dried for 12 hours at 120° C. The BHET was free of any catalysts and additives and had a degree of esterification of approximately 91%, a free acid content of approximately 900 mmol/kg and an amount of unreacted PTA of approximately 200 mmol/kg. The 50 g BHET was filled into the 60 ml glass flask reactor. Then 0.485 ml triethylphosphate as 1.00 w/w % solution in ethylene glycol was filled into the reactor together with 5 g monoethyleneglycol to flush all raw materials completely into the reactor.

The 60 ml glass flask reactor was then dipped into a salt bath and the nitrogen purge was opened. The heating of the salt bath was set to 265° C. and after 15 min of melting the stirrer was set from manual operation to continuous agitation at 200 rpm. After additional 15 min, in total 30 min after the start of heating, 21.48 mg pure antimony triglycolate powder was added and the pressure was reduced over 15 min from atmospheric pressure to approximately 10 mbar. After an additional 15 min, in total 45 min after the start of heating, time zero was defined for following hourly sampling. Pressure was reduced over the next 15 min to approximately 1 mbar. After an additional 15 min, in total 60 min after the start of heating, the temperature of the salt bath was set from 265 to 283° C. One hour after time zero, or 1 hour and 45 minutes after the start of heating, the first sample of approximately 2 grams was sampled of the reactor with a wire after the reactor was pressurised with nitrogen to atmospheric pressure and the stirrer was set from 200 to 100 rpm. After the sample was taken the pressure was again set to approximately 1 mbar. The same procedure was carried out for taking a sample after two and three hours after time zero. The sample after three hours was split and one part was used for the degradation procedure.

EXAMPLE B

Example B is the standard titanium reference performance in a batch reactor. The standard Ti-catalyst was VERTEC®TIPT, 97+w/w % purity, as citrate. Final content of titanium (Ti) was calculated to be 9.6 ppm and phosphorus (P) was calculated with 20 ppm in the finished polymer. The ratio of BHET to final polymer was calculated with 210/192.

A polyester polycondensation reaction is performed in a 60 ml glass flask reactor which is equipped additionally with a glass stirrer, a side glass tube for taking samples, a 50 ml glass flask connected to the top of the 60 ml glass flask to collect the off diol, a connection to purge nitrogen and a connection to vacuum.

50 g of bis-2-hydroxy-ethylene-terephthalate (BHET), the esterification product from the reaction of the dicarboxylic acid terephthalic acid and the diol monoethyleneglycol, was ground to approximately 3 mm size and were dried for 12 hours at 120° C. The BHET was free of any catalysts and additives and had a degree of esterification of approximately 91%, a free acid content of approximately 900 mmol/kg and an amount of unreacted PTA of approximately 200 mmol/kg. The 50 g BHET was filled into the 60 ml glass flask reactor. Then 0.485 ml triethylphosphate as 1.00 w/w % solution in ethylene glycol were filled into the reactor together with 5 g monoethyleneglycol to flush all raw materials completely into the reactor.

The 60 ml glass flask reactor was then dipped into a salt bath and the nitrogen purge was opened. The heating of the salt bath was set to 265° C. and after 15 min of melting the stirrer was set from manual operation to agitation at 200 rpm. After an additional 15 min, in total 30 min after the start of heating, 0.800 ml of 1 w/w % Ti containing standard Ti citrate catalyst 1 was added and the pressure was reduced over the next 15 min from atmospheric pressure to approximately 10 mbar. After an additional 15 min, in total 45 min after the start of heating, time zero was defined for following hourly sampling. Pressure was reduced over the next 15 min to approximately 1 mbar. After an additional 15 min, in total 60 min after the start of heating, the temperature of the salt bath was set from 265 to 283° C. One hour after time zero, or 1 hour and 45 minutes after the start of heating, the first sample of approximately 2 grams was sampled of the reactor with a wire after the reactor was pressurised with nitrogen to atmospheric pressure and the stirrer was set from 200 to 100 rpm. After the sample was taken the pressure was again set to approximately 1 mbar. The same procedure was followed for taking a sample after two and three hours after time zero. The sample after three hours was split and one part was used for the degradation procedure.

EXAMPLE C

Example C is the high purity titanium citrate catalyst 3 performance in a batch reactor. The high purity titanium catalyst was IG Ultra-Pure TIPT, 99.8+w/w % purity, as citrate from Catalytic Technologies Ltd. Final content of titanium (Ti) was calculated with 9.6 ppm and phosphorus (P) was calculated with 20 ppm in the finished polymer. The ratio of BHET to final polymer was calculated with 210/192.

A polyester polycondensation reaction is performed in a 60 ml glass flask reactor which is equipped additionally with a glass stirrer, a side glass tube for taking samples, a 50 ml glass flask connected to the top of the 60 ml glass flask to collect the off diol, a connection to purge nitrogen and a connection to vacuum.

50 g of bis-2-hydroxy-ethylene-terephthalate (BHET), the esterification product from the reaction of the dicarboxylic acid terephthalic acid and the diol monoethyleneglycol, was ground to approximately 3 mm size and was dried for 12 hours at 120° C. The BHET was free of any catalysts and additives and had a degree of esterification of approximately 91%, a free acid content of approximately 900 mmol/kg and an amount of unreacted PTA of approximately 200 mmol/kg. The 50 g BHET was filled into the 60 ml glass flask reactor. Then 0.485 ml triethylphosphate as 1.00 w/w % solution in ethylene glycol was filled into the reactor together with 5 g monoethyleneglycol to flush all raw materials completely into the reactor.

The 60 ml glass flask reactor was then dipped into a salt bath and the nitrogen purge was opened. The heating of the salt bath was set to 265° C. and after 15 min of melting the stirrer was set from manual operation to agitation at 200 rpm. After an additional 15 min, in total 30 min after the start of heating, 0.800 ml of 1 w/w % Ti containing high purity Ti citrate catalyst 3 was added and the pressure was reduced over the next 15 min from atmospheric pressure to approximately 10 mbar. After an additional 15 min, in total 45 min after the start of heating, time zero was defined for following hourly sampling. The pressure was reduced over the next 15 min to approximately 1 mbar. After an additional 15 min, in total 60 min after the start of heating, the temperature of the salt bath was set from 265 to 283° C. One hour after time zero, or 1 hour and 45 minutes after the start of heating, the first sample of approximately 2 grams was sampled of the reactor with a wire after the reactor was pressurised with nitrogen to atmospheric pressure and the stirrer was set from 200 to 100 rpm. After the sample was taken the pressure was again set to approximately 1 mbar. The same procedure was carried out for taking a sample after two and three hours after time zero. The sample after three hours was split and one part was used for the degradation procedure.

|  |  | Example A<br>Standard Antimony<br>270 ppm Sb,<br>20 ppm P | Example B<br>Standard Titanium<br>9.6 ppm std. Ti,<br>20 ppm P | Example C<br>Purified Titanium<br>9.6 ppm pur. Ti,<br>20 ppm P |  |
|---|---|---|---|---|---|
| IV BHET | dl/g | ~0.05 | ~0.05 | ~0.05 | IV = intrinsic viscosity |
| IV 1 h | dl/g | 0.586 | 0.486 | 0.574 | 1 h = sampling after one hour |
| IV 2 h | dl/g | 0.752 | 0.729 | 0.711 | 2 h = sampling after two hours |
| IV 3 h | dl/g | 0.776 | 0.710 | 0.776 | 3 h = sampling after three hours |
| IV 3 h+ | dl/g | 0.485 | 0.580 | 0.581 | 3 h+ = degradation procedure |

-continued

|  |  | Example A<br>Standard Antimony<br>270 ppm Sb,<br>20 ppm P | Example B<br>Standard Titanium<br>9.6 ppm std. Ti,<br>20 ppm P | Example C<br>Purified Titanium<br>9.6 ppm pur. Ti,<br>20 ppm P |  |
|---|---|---|---|---|---|
| delta IV | dl/g/min | −0.0291 | −0.0130 | −0.0195 | delta IV = (IV 3 h+ − IV 3 h)/10 |
| L* BHET | CIE-LAB | 96.6 | 96.6 | 96.6 | L* = L* colour |
| L* 1 h | CIE-LAB | 86.1 | 91.3 | 89.5 | 1 h = sampling after one hour |
| L* 2 h | CIE-LAB | 84.3 | 88.6 | 88.2 | 2 h = sampling after two hours |
| L* 3 h | CIE-LAB | 86.4 | 87.1 | 88.9 | 3 h = sampling after three hours |
| L* 3 h+ | CIE-LAB | 85.8 | 80.7 | 86.3 | 3 h+ = degradation procedure |
| delta L* | units/min | −0.1 | −0.6 | −0.3 | delta L* = (L* 3 h+ − L* 3 h)/10 |
| a* BHET | CIE-LAB | −0.3 | 0.3 | −0.3 | a* = a* colour |
| a* 1 h | CIE-LAB | −0.7 | −1.6 | −1.4 | 1 h = sampling after one hour |
| a* 2 h | CIE-LAB | −0.8 | −2.2 | −1.5 | 2 h = sampling after two hours |
| a* 3 h | CIE-LAB | −1.2 | −1.6 | −1.9 | 3 h = sampling after three hours |
| a* 3 h+ | CIE-LAB | −2.6 | −0.2 | −2.9 | 3 h+ = degradation procedure |
| delta a* | units/min | −0.1 | 0.1 | −0.1 | delta a* = (a* 3 h+ − a* 3 h)/10 |
| b* BHET | Minolta | 1.4 | 1.4 | 1.4 | b* = b* colour |
| b* 1 h | Minolta | 3.8 | 4.8 | 6.0 | 1 h = sampling after one hour |
| b* 2 h | Minolta | 4.8 | 7.5 | 7.6 | 2 h = sampling after two hours |
| b* 3 h | Minolta | 7.2 | 17.0 | 11.2 | 3 h = sampling after three hours |
| b* 3 h+ | Minolta | 10.3 | 18.7 | 13.0 | 3 h+ = degradation procedure |
| delta b* | units/min | 0.3 | 0.2 | 0.2 | delta b* = (b* 3 h+ − b* 3 h)/10 |
| AA 3 h | ppm | 25.4 | 18.9 | 16.8 | 3 h = sampling after three hours |
| AA 3 h+ | ppm | 44.6 | 55.8 | 19.5 | 3 h+ = degradation procedure |
| delta AA | ppm/min | 1.9 | 3.7 | 0.3 | delta AA = (AA 3 h+ − AA 3 h)/10 |
| COOH 3 h | mmol/kg | 55 | 63 | 38 | 3 h = sampling after three hours |
| COOH 3 h+ | mmol/kg | 78 | 99 | 60 | 3 h+ = degradation procedure |
| delta COOH | mmol/kg/min | 2.3 | 3.6 | 2.2 | delta COOH = (COOH 3 h+ − COOH 3 h)/10 |

2.4. Continuous Process Experiments

EXAMPLE D

Example D is the standard antimony catalyst performance in a state of the art continuous process. The standard antimony was Youngsun® Antimony Glycolate from Antraco. In a continuous polyester pilot line a main dicarboxylic acid, a second dicarboxylic acid and a diol was first esterified then prepolycondensed and finally polycondensed to a high viscosity polyester, referred to as final polymer of the melt phase.

Purified terephthalic acid (PTA), purified isophthalic acid (PIA) and mono ethylene glycol (EG) were prepared batch wise in an agitated preparation vessel as a paste mixture and were fed batch wise into an agitated paste feed vessel. One paste batch was prepared from 500 kg PTA, 11.9 kg PIA, 363 kg EG and 126 g triethylphosphate (TEP). For 50 kg/h PET polyester a mass flow of 73.5 kg/h of the paste was calculated. At 73.5 kg/h paste mass flow the 126 g TEP per paste batch were calculated to result in 10 ppm elemental phosphorus (P) referred to polymer of the melt phase. The 11.9 kg PIA per paste batch was calculated to 2.0 w/w % referred to polymer of the melt phase.

From the paste feed vessel a paste mass flow of 73.5 kg/h was fed continuously into an esterification vessel. The esterification vessel had an outside heat exchanger, connected to the esterification vessel via a circulation loop. The heat exchanger was operated with a heat transfer medium (HTM) at approximately 296° C. to ensure a constant esterification product temperature of approximately 274° C. Reaction water and excess ethylene glycol were released at 260 kPa via a vapour pipe into a distillation column. In this esterification reaction mainly bis-2-hydroxy-ethylene-glycol (BHET), also called monomer or oligomer, was formed by autocatalysis and had a degree of esterification of 92-94%, a free acid content of 550-720 mmol/kg and an amount of unreacted PTA of 0-100 mmol/kg.

A constant level of approximately 72% in the esterification vessel, which relates to approximately 108 minutes hold up time, was kept by a continuous product feed from the esterification vessel to a cascade of four reaction vessels to finish the esterification reaction and to start the polycondensation reaction. The four vessels were heated with a heat transfer medium at approximately 284° C. to ensure a constant product temperature of approximately 276° C. Reaction water and excess ethylene glycol were released at 70 kPa via a vapour pipe into a condenser. The standard antimonytriglycolate catalyst 1 was fed into the first vessel as a 2.0 w/w % solution in ethylene glycol with a flow of 1.20 kg/h for 50 kg/h final polyester polymer. The antimony content in the final polyester polymer was calculated as 250 ppm. The first three vessels had an overflow to the next vessel and the fourth vessel was controlled at a constant level of about 30%, which related in total to approximately 62 min hold up time. After these four vessels the product had a degree of esterification of 98.5-99.5%, and a free acid content of 100-160 mmol/kg. Triethylphosphate (TEP) was fed into the continuous product flow from the fourth vessel at 20 w/w % in ethylene glycol at 13.5 ml/h. Together with the TEP in the paste feed, a total phosphorus content in the final polyester polymer was calculated at 20 ppm.

The product flow from the fourth vessel was fed into a pre-polycondensation reactor, designed as vertical pipes which build up a thin product fall film with high reaction surface and followed by a collector vessel. The reactor was heated with a heat transfer medium at approximately 286° C. to ensure a constant product temperature of approximately 282° C. Excess ethylene glycol was released at 1.5 kPa via a vapour pipe into a condenser. The level of the collector vessel was kept constant at approximately 48%, which related in total to approximately 30 min hold up time for the pre-polycondensation reaction and resulted in a product with 40-60 mmol/kg COOH end groups and an IV of 0.27-0.29 dl/g.

The product from the pre-polycondensation reaction was fed continuously into a polycondensation reactor. This reactor was a horizontal reactor with a rotating discs agitator at a speed of 1.6 rpm and rotating wipers at a speed of 0.9 rpm. The reactor was controlled at an inlet level of approximately 14% and a weight measurement which indicated a hold up time of approximately 94 minutes. The reactor was heated with a heat transfer medium at approximately 295° C. to ensure an inlet product temperature of approximately 284° C. and an outlet product temperature of approximately 285° C. Excess ethylene glycol was released at 0.079 kPa via a vapour pipe into a condenser. The product from the polycondensation reactor was discharged via a gear pump at constant speed for 50 kg/h final polyester polymer into a state of the art underwater granulator. The cut granulates were separated from the water via a centrifugal dryer and directly transferred at approximately 120-140° C. into a silo. Amorphous granulate samples were taken directly after the centrifugal dryer.

The properties of the final polyester polymer were as follows:

|  | IV | COOH | AA | Colour CIE-LAB | | |
|---|---|---|---|---|---|---|
|  | dl/g | mmol/kg | ppm | L* | a* | b* |
| Before degradation procedure | 0.88 | 23.6 | 26.8 | 90.0 | −1.1 | 4.0 |
| After degradation procedure | 0.70 | 50.7 | 54.9 | 79.9 | −1.9 | 7.9 |

EXAMPLE E

Example E is the high purity titanium citrate catalyst 3 performance in a state of the art continuous process. In a continuous polyester pilot line a main dicarboxylic acid, a second dicarboxylic acid and a diol was first esterified then prepolycondensed and finally polycondensed to a high viscosity polyester, called final polymer of the melt phase.

Purified terephthalic acid (PTA), purified isophthalic acid (PIA) and mono ethylene glycol (EG) were prepared batch wise in an agitated preparation vessel as a paste mixture and were fed batch wise into an agitated paste feed vessel. One paste batch was prepared from 500 kg PTA, 11.9 kg PIA, 363 kg EG and 126 g triethylphosphate (TEP). For 50 kg/h PET polyester a mass flow of 73.5 kg/h of the paste was calculated. At 73.5 kg/h paste mass flow the 126 g TEP per paste batch was calculated to result in 10 ppm elemental phosphorous (P) referred to polymer of the melt phase. The 11.9 kg PIA per paste batch was calculated to 2.0 w/w % referred to polymer of the melt phase.

From the paste feed vessel a paste mass flow of 73.5 kg/h was fed continuously into an esterification vessel. The esterification vessel had an outside heat exchanger, connected to the esterification vessel via a circulation loop. The heat exchanger was operated with a heat transfer medium (HTM) at approximately 296° C. to ensure a constant esterification product temperature of approximately 274° C. Reaction water and excess ethylene glycol were released at 260 kPa via a vapour pipe into a distillation column. In this esterification reaction mainly bis-2-hydroxy-ethylene-glycol (BHET), also called monomer or oligomer, was formed by autocatalysis and had a degree of esterification of approximately 92-94%, a free acid content of 550-720 mmol/kg and an amount of unreacted PTA of 0-100 mmol/kg.

A constant level of approximately 72% in the esterification vessel, which relates to approximately 108 minutes hold up time, was kept by a continuous product feed from the esterification vessel to a cascade of four reaction vessels to finish the esterification reaction and to start the polycondensation reaction. The four vessels were heated with a heat transfer medium at approximately 284° C. to ensure a constant product temperature of approximately 276° C. Reaction water and excess ethylene glycol were released at 70 kPa via a vapour pipe into a condenser. High purity titanium citrate catalyst 3 was fed into the first vessel as a 0.83 w/w % solution in ethylene glycol with a flow of 1.10 kg/h for 50 kg/h final polyester polymer. The titanium content in the final polyester polymer was calculated at 9 ppm. The first three vessels had an overflow to the next vessel and the fourth vessel was controlled at a constant level of approximately 30%, which related in total to approximately 62 min hold up time. After these four vessels the product had a degree of esterification of approximately 98.5-99.5%, and a free acid content of 100-160 mmol/kg. Triethylphosphate (TEP) was fed into the continuous product flow from the fourth vessel at 20 wt % in ethylene glycol at 13.5 ml/h. Together with the TEP in the paste feed, a total phosphorus content in the final polyester polymer was calculated at 20 ppm.

The product flow from the fourth vessel was fed into a pre-polycondensation reactor, designed as vertical pipes which build up a thin product fall film with high reaction surface and followed by a collector vessel. The reactor was heated with a heat transfer medium at approximately 286° C. to ensure a constant product temperature of approximately 282° C. Excess ethylene glycol was released at 1.5 kPa via a vapour pipe into a condenser. The level of the collector vessel was kept constant at approximately 48%, which related in total to approximately 30 min hold up time for the pre-polycondensation reaction and resulted in a product with 40-60 mmol/kg COOH end groups and an IV of 0.27-0.29 dl/g.

The product from the pre-polycondensation reaction was fed continuously into a polycondensation reactor. This reactor was a horizontal reactor with a rotating discs agitator at a speed of 1.6 rpm and rotating wipers at a speed of 0.9 rpm. The reactor was controlled at an inlet level of approximately 13% and a weight measurement which indicated a hold up time of approximately 83 minutes. The reactor was heated with a heat transfer medium at approximately 295° C. to ensure an inlet product temperature of approximately 284° C. and an outlet product temperature of approximately 285° C. Excess ethylene glycol was released at 0.048 kPa via a vapour pipe into a condenser. The product from the polycondensation reactor was discharged via a gear pump at constant speed for 50 kg/h final polyester polymer into a state of the art underwater granulator. The cut granulates were separated from the water via a centrifugal dryer and directly transferred at approximately 120-140° C. into a silo. Amorphous granulate samples were taken directly after the centrifugal dryer.

The properties of the final polyester polymer were as follows:

|  | IV | COOH | AA | Colour CIE-LAB | | |
|---|---|---|---|---|---|---|
|  | dl/g | mmol/kg | ppm | L* | a* | b* |
| Before degradation procedure | 0.83 | 27.8 | 27.3 | 88.2 | −1.7 | 3.8 |
| After degradation procedure | 0.66 | 42.8 | 34.8 | 81.8 | −2.5 | 6.9 |

Comparison of example D and E

|  | delta IV dl/g/min | delta COOH mmol/kg/min | delta AA ppm/min | Colour CIE-LAB | | |
|---|---|---|---|---|---|---|
|  |  |  |  | delta L*/min | delta a*/min | delta b*/min |
| Standard Sb catalyst | −0.018 | 2.7 | 2.8 | −1.0 | −0.1 | 0.4 |
| Purified Ti catalyst | −0.017 | 1.5 | 0.8 | −0.6 | −0.1 | 0.3 |

Delta IV=(IV after degradation procedure−IV before degradation procedure)/10 min
Delta COOH=(COOH after degradation procedure−COOH before degradation procedure)/10 min
Delta AA=(AA after degradation procedure−AA before degradation procedure)/10 min
Delta L*=(L* after degradation procedure−L* before degradation procedure)/10 min
Delta a*=(a* after degradation procedure−a* before degradation procedure)/10 min
Delta b*=(b* after degradation procedure−b* before degradation procedure)/10 min

EXAMPLE F

Granulate from example D (the granulate from the continuous process with the standard antimony catalyst) was taken directly from the centrifugal dryer of the under water granulation at a temperature of approximately 120-140° C. and fed into a conditioning silo to remove most of the acetaldehyde. The conditioning process in the conditioning silo was carried out for 12 hours at atmospheric pressure with a temperature profile from 120° C. at the silo inlet to 180° C. at the silo outlet, before the granulate was cooled down in a heat exchanger to approximately 50° C. The temperature increase was realised by the latent heat energy during crystallisation and a jacket heating of the silo of 180° C. To avoid an explosive atmosphere of volatile acetaldehyde and ethylene glycol a small amount of air (20 kg/h at 30° C., with a dew point of about −50° C.) was fed into the bottom of the silo. The granulate from the silo was then taken to make a preform, a precursor for a final bottle, using a re-extrusion process.

The preform process was performed with a Netstal S-1000-460/-60 extruder with a screw of 45 mm diameter, a temperature profile for melting of the granulates of 270° C. at the inlet to 290° C. before the die head and 300° C. at the die head. The total hold-up time in the extruder was 4 minutes. The preforms had a weight of 39.1 g and the results are as follows:

|  | IV dl/g | COOH mmol/kg | AA ppm | Colour CIE-LAB | | |
|---|---|---|---|---|---|---|
|  |  |  |  | L* | a* | b* |
| After conditioning silo | 0.91 | 24 | 0.7 | 85.0 | −1.8 | 3.6 |
| After re-extrusion, preform | 0.86 | 32 | 4.5 | 81.5 | −1.9 | 4.7 |
| Delta due to degradation | −0.05 | 8 | 3.8 |  |  |  |

The colour values have to be considered carefully from before and after re-extrusion because after conditioning silo the granulates were crystallised and the colour values from the preforms were measured after grinding of the amorphous preforms therefore no delta is calculated.

EXAMPLE G

Granulate from example E (the granulate from the continuous process with the high purity titanium citrate catalyst 3) was taken directly from the centrifugal dryer of the under water granulation at a temperature of approximately 120° C. and fed into a conditioning silo to remove most of the acetaldehyde. The conditioning process in the conditioning silo was carried out for 12 hours at atmospheric pressure with a temperature profile from 120-140° C. at the silo inlet to 180° C. at the silo outlet before the granulate was cooled down in a heat exchanger to approximately 50° C. The temperature increase was realised by the latent heat energy during crystallisation and a jacket heating of the silo to 180° C. To avoid an explosive atmosphere of volatile acetaldehyde and ethylene glycol a small amount of air (20 kg/h at 30° C., with a dew point of approximately −50° C.) was fed into the bottom of the silo. The granulate from the silo was then taken to make a preform, a precursor for a final bottle, using a re-extrusion process.

The preform process was performed with a Netstal S-1000-460/-60 extruder with a screw of 45 mm diameter, a temperature profile for melting of the granulates of 270° C. at the inlet to 290° C. before the die head and 300° C. at the die head. The total hold-up time in the extruder was 4 minutes. The preforms had a weight of 39.1 g and the results are as follows:

|  | IV dl/g | COOH mmol/kg | AA ppm | Colour CIE-LAB | | |
|---|---|---|---|---|---|---|
|  |  |  |  | L* | a* | b* |
| After conditioning silo | 0.85 | 28 | 0.5 | 80.0 | −2.6 | 1.5 |
| After re-extrusion, preform | 0.82 | 31 | 3.1 | 80.7 | −1.8 | 2.6 |
| Delta due to degradation | −0.03 | 3 | 2.6 |  |  |  |

The colour values have to be considered carefully from before and after re-extrusion because after the conditioning silo the granulates were crystallised and the colour values from the preforms were measured from the amorphous preforms therefore no delta is calculated.

Comparison of Example F and G

|  | Delta IV dl/g | Delta COOH mmol/kg | Delta AA ppm | Colour CIE-LAB | | |
|---|---|---|---|---|---|---|
|  |  |  |  | L* | a* | b* |
| Preform with standard antimony catalyst | −0.05 | 8 | 3.8 | 81.5 | −1.9 | 4.7 |
| Preform with high purity titanium citrate catalyst 3 | −0.03 | 3 | 2.6 | 80.7 | −1.8 | 2.6 |

Delta IV = (IV before re-extrusion−IV after re-extrusion)
Delta COOH = (COOH before re-extrusion−COOH after re-extrusion)
Delta AA = (AA before re-extrusion−AA after re-extrusion)

The colour values can be compared as both preform colours were measured as amorphous preforms.

2.5 Examination Methods
2.5.1. Thermal Degradation Procedure

To simulate thermal degradation during re-extrusion the following procedure was used. Approximately 10 g of solid polyester is ground to powder in a mill at room temperature until an average particle size of below 1 mm is achieved. This powder is then placed into an oven for 16 hours at 140° C.±3° C. to ensure a water content below 30 ppm $H_2O$ in the polyester in order to avoid degradation by hydrolysis at the higher temperatures later used. After drying the polyester powder at 140° C. it is immediately transferred to a test tube. The test tube is then continuously blanketed with inert nitrogen gas and immediately lowered into a salt bath of 290° C.±1° C. for 10 minutes while slightly swinging the test tube but without any extra agitation. After exactly 10 min the test tube is placed with slight swinging into dry ice for rapid cooling. The final solid polyester is then taken for further analysis.

2.5.2. Determination of the Relative Solution Viscosity (IV)

The determination of the solution viscosity of polyester samples is a standard method in the quality control for production and processing of PET. The calculated intrinsic viscosity correlates to the degree of polycondensation and the molecular weight. The principle is to dissolve a sample in a solution, here a mixture of phenol and 1,2-dichlorobenzene, and the flow time of the solution in a capillary viscometer is determined at a certain temperature, here 25° C.

200 mg±0.2 mg of the sample, which has a water content below 0.5 wt %, is weighed into a 50 ml narrow neck Erlenmeyer flask. Add a magnetic stirring bar and 40.0 ml of the solvent mixture of phenol/1,2-dichlorobenzene (1:1 by weight) with a volumetric pipette and close the flask with a stopper loosely. Place the flask into the preheated aluminium block of the magnetic stirrer and dissolve the sample under stirring at 130° C. for 30 minutes until all the PET has dissolved. Cool down the sample to ambient temperature and filter the solution through a glass filter funnel into the Ubbelohde capillary.

Place the capillary into the thermostatic water bath (25.0±0.1° C.) and let it stand for 15 minutes before starting the measurement. Determine the flow time the solution needs to flow from the upper to the lower measuring mark). Repeat the measurement until five consecutive time readings are differing less than 0.2 s. In the same way the flow time of the pure solvent mixture of phenol/1,2-dichlorobenzene (1:1 by weight) $t_0$ has to be determined for every viscometer once a week or after a new solvent mixture is used.

Typically a correction time must be considered for the obtained average values of the flow times of the pure solvent mixture ($t_0$) as well as the sample solution (t). The correction time $\Delta t$ (Hagenbach-Couett correction) eliminates the influence of the gravitation to the viscosity determination. The correction time values $\Delta t$ are read from the operating instructions of the viscometer.

The relative viscosity $\eta_{rel}$ of the sample is obtained from the following equation:

$$\eta_{rel} = \frac{t - \Delta t}{t_0 - \Delta t_0}$$

t: flow time of sample [s]
$\Delta t$: Hagenbach correction time for the sample [s]
$t_0$: flow time of pure solvent mixture [s]
$\Delta t_0$: Hagenbach correction time for pure solvent mixture [s]

The result is reported in three significant figures. The intrinsic viscosity (IV) number is calculated according to the following equation:

$$IV = \frac{-1 + \sqrt{1 + 4*KH*\eta_{spec}}}{2*KH*c} [dl/g]$$

KH: HUGGINS constant; for PET according to this procedure KH=0.33
$\eta_{spec}$: specific viscosity number $\eta_{spec} = \eta_{rel} - 1$
c: concentration of PET-sample; c=E/400 [g/dl]
E: mass of the sample weighed in [mg]

2.5.3 Determination of the Carboxyl End Group Content (COOH)

The determination of the carboxylic end group content (CEG) is a standard method in the quality control for the production and processing of polyesters. The content of carboxylic end groups influences the thermal stability of polyester. The sample is dissolved in phenol/chloroform (1:1) at 80° C. and titrated with a 0.1 N solution of potassium hydroxide in benzyl alcohol against tetrabromophenol blue as an indicator.

Factor Determination of the 0.1 N Benzyl Alcoholic KOH Solution:

Weigh into a 250 ml Erlenmeyer flask 100-120 mg (accuracy ±0.1 mg) of benzoic acid (Z) and add 50 ml ethanol. After addition of a few drops of 1.0% ethanolic phenolphthalein solution titrate the mixture with 0.1 N benzylalcoholic KOH solution to the appearance of a permanent pink colour (E). Run a blank with 50 ml ethanol (D). Perform at least a double determination for the benzoic acid solution and blank. The factor f of the 0.1 N benzylalcoholic KOH-solution is calculated according to:

$$f = \frac{10*Z}{(E - D)*122,1}$$

Z: Mass of benzoic acid weighed in [mg]
E: Volume of 0.1 N benzylalcoholic KOH-solution required for benzoic acid titration [ml]
D: Volume of 0.1 N benzylalcoholic KOH-solution required for blank titration [ml]
10: Theoretical consumption of 0.1 N KOH [ml/mmol] for 122.1 mg benzoic acid
122.1: Molecular weight of benzoic acid [g/mol]

Determination of the Carboxyl End Group Content:

Weigh 3-4 g of chips (W, accuracy ±1 mg) into a 100 ml Erlenmeyer flask, add 50 ml of the phenol/chloroform mixture, some boiling aids and reflux for approximately 1 h until a clear solution is obtained. To protect the sample and blank against atmospheric $CO_2$, the reflux condenser must be equipped with a soda lime tube. After cooling down to room temperature add under stirring 0.5 ml of 0.1% tetrabromophenol blue solution. The obtained yellow coloured solution is then titrated with 0.1 N benzyl alcoholic KOH solution to a distinct blue colour (colour changes from yellow to blue through green). Note the amount of 0.1 N benzyl alcoholic KOH-solution consumed (A) and determine a blank value prepared under identical conditions without the sample (B). For better comparison of a filled/matted sample against the blank, add a small amount of $TiO_2$ to the blank. The sample must be titrated until the colour of the sample is identical to the blank.

Perform at least double determinations of sample and blank.

The content of carboxylic end groups (COOH or CEG) of a polyester sample is calculated according to:

$$COOH = \frac{(A - B)*f*100}{W} [mmol/kg]$$

A: Volume of 0.1 N benzyl alcoholic KOH-solution required for the sample [ml]
B: Volume of 0.1 N benzyl alcoholic KOH-solution required for the blank [ml]
f: Factor of the benzyl alcoholic KOH-solution
W: Mass of sample weighed in [g]

Reported is the average value of the sample determinations.

2.5.4. Determination of Acetaldehyde (AA) Content in Polyester Chips or Preform Samples.

The AA content is of special interest in the production of PET-bottles. AA is desorbed from a grinded polyester sample during heating in a sealed vial at 150° C. for 60 min. The gas phase formed above the sample (head space) is analysed by gas-chromatography (GC). For calibration of the AA content in PET external standards are used.

Used equipment: Gas chromatograph (GC) equipped with flame ionisation detector (FID) and evaluation software and as column: FS-CW-20M-CB-0.25 (25 m×0.32 mm) or J & W Scientific GS-Q 115-3432 (30 m×0.53 mm).

GC conditions: carrier gas $N_2$ at 60 kPa, injector 250° C., split ratio 10:1, detector FID at 280° C., air at 450 ml/min, $H_2$ at 45 ml/min, program 90° C. (isothermal), run time: 8 min.

Headspace conditions: oven temperature 150° C., needle temperature 160° C., transfer line temperature 170° C., injections per vial 1, thermostating time 60 min, carrier gas pressure 90 kPa, vial pressure 90 kPa, pressurization time 0.2 min, injection time 0.1 min, withdrawal time 0 min, GC-cycle time 30 min.

Calibration: prepare in a 100 ml volumetric flask a stock solution of approx. 1 g AA (accuracy ±1 mg) in benzyl alcohol or iso-propanol (solvent). Take care that AA is chilled to near 0° C. before it is transferred to the volumetric flask. Have approx. 20 ml of solvent present in the volumetric flask before adding the AA. Close the stopper immediately after the addition of the AA and note the amount of AA present in the solution, then add solvent close to the mark. After thermostating at 20.0° C. fill up to the mark. Transfer exactly 10 ml of the stock solution to a 100 ml volumetric flask and dilute to the mark with solvent after thermostating (=standard solution). Prepare at least 15 empty headspace vials and with the syringes inject different volumes of the standard solution into the open vials. Select volumes between 0.5 and 20 µl of standard solution (approx. 0.5-20 µg AA or 2.5-100 ppm respectively) depending on the expected amount of AA in PET. Before addition of a defined volume of standard solution to a headspace vial smear excess liquid that is on the syringe tip on the outside of the vial. Place the syringe inside the vial that the tip touches the bottom or the wall, then quickly inject the volume and swirl the syringe tip around the inside of the vial to smear all liquid on the vial walls. Remove the syringe and immediately cap the vial. Prepare at least a triple determination of each calibration level. If higher or lower AA-contents are expected, use a differently diluted standard solution for the calibration. Insert the vials into the headspace unit of the GC and perform the analysis according to the GC/headspace conditions. For the calibration plot the area read from the peak corresponding to AA over the amount of AA (µg) contained in the volume of standard solution transferred to the headspace vials. Calculate the calibration curve as the regression line according to the root mean square method and make sure that the calibration curve is forced through the origin (include zero point).

Sample determination: Precool the polyester sample in liquid $N_2$ or solid $CO_2$, then grind the sample in the grinding mill with a 750 µm sieve attached. Allow the ground sample to come to room temperature (approx. 10 min.), then weigh in approx. 0.2 g±0.02 g into an empty headspace vial which is immediately sealed with a septum and cap (E). Insert the vial into the headspace unit of the GC and perform the analysis of the AA content according to the GC/headspace conditions. Make at least a double determination for each sample and calculate the average value.

Note: If the ground samples cannot be analysed immediately, store in a tightly closed vial in a freezer at −20° C. until analysis.

Results: Identification of AA in the chromatograms is made according to the retention time. From the obtained peak area the corresponding amount of AA [µg] is read from the calibration curve. The content of AA in the polyester sample is calculated according to:

Acetaldehyde=AA/E [ppm]

AA: amount of AA in the sample read from the calibration curve [µg]
E: mass of polyester sample weighed in [g]

2.5.6 Determination of the Colour Values (L*, a*, b*) (CIE-LAB) of Ground Polyester Pellets The colour of a sample can be influenced by its thermal history or due to oxidative damage. Light coming from a standard light source is reflected from the surface of a ground PET sample. The intensity of the reflected light is determined photo electrically with a colour spectrophotometer calibrated to a white standard. The obtained colour values are reported in the CIE-LAB system.

Colour spectrophotometer, measurement of reflectance, 400-700 nm, d/8°, aperture 10 mm.

Prior to the determination set up the spectrophotometer according to the operating manual and use the following settings: Standard illumination type D65, Standard Observer 10°, Gloss included (no gloss subtraction), Colour measurement L*a*b*, Calibrate the instrument with the standard plate(s) according to the manual.

Before starting the measurement make sure that the bottom of the glass cells are absolutely clean and free from adhering dust particles or fingerprints. Otherwise clean carefully with ethanol/acetone using a tissue and blow dry with forced air or nitrogen. Then fill the cell with ground pellets up to a height of approx. 1 cm. Tap at the edges of the cell to distribute the polymer homogeneously and to avoid voids. Place the cell on the measuring aperture of the spectrophotometer and perform the determination of the colour values according to the operating manual. Repeat the determination three times, each time after turning the glass cell with the sample in an angle of approx. 90°. Discard the sample and repeat the measurement with a new amount of the ground pellets. Measure at least three different fillings of each sample and calculate and report the average values.

2.5.7 Determination of the degree of esterification

This method is applied to determine the saponification number (SN) of PET esterification products. From the SN and the content of carboxylic end groups (Free Acid—FA) in a sample the degree of esterification can be calculated. Grinded esterification product is saponified with potassium hydroxide (KOH), the amount of KOH not consumed is titrated back with hydrochloric acid solution (HCl) against phenolphthalein.

Prior to the determination prepare a 250 ml flask by boiling in 2.5% KOH solution for several minutes then rinse thoroughly with water and let dry. Weigh into a prepared 250 ml flask 0.2-0.3 g of finely ground sample (W, accuracy ±1 mg), then add 40 ml of 0.5 N KOH solution and 40 ml of ethylene glycol. Attach the reflux condenser equipped with a soda lime tube and heat the solution under stirring and refluxing until all sample material has dissolved (about 2 h; a slight turbidity may remain from undissolved $TiO_2$). After the solution has cooled down to room temperature add approx. 5 drops of 1.0% phenolphthalein solution and titrate with 0.5 N HCl solution until the pink colour has disappeared (V). If the end-point of the titration is difficult to determine, compare against a fully titrated solution for control. Make at least a double determination.

A blank determination using the given procedure with identical amounts of 0.5 N KOH solution and ethylene glycol has to be performed each time. Perform a double determination and determine the volume of 0.5 N HCl solution consumed (VB). The saponification number (SN) of the sample is calculated according to:

$$SN = \frac{(V_B - V * f * 0.5)}{W} \text{ [mmol/g]}$$

$V_B$: Volume of 0.5 N HCl-solution required for blank [ml]
V: Volume of 0.5 N HCl-solution required for sample [ml]
f: Factor of 0.5 N HCl-solution
W: Mass of the sample weighed in [g]

The invention claimed is:

1. A titanium containing catalyst comprising one or more titanium alpha-hydroxy carboxylate species and one or more titanium oxide species of the formula $TiO_x$, wherein x is greater than 0 and less than or equal to 2, wherein the sum of all of the titanium oxide species relative to the sum of all titanium alpha-hydroxy carboxylate species is greater than 0 but less than 1.00 mol.-%,
wherein the titanium containing catalyst is produced by a method comprising reacting at least one alpha-hydroxy carboxylic acid with titanium-(IV)-isopropoxide having a purity of 99.8 wt/wt % or higher, at a molar ratio of the at least one alpha-hydroxy carboxylic acid relative to the titanium-(IV)-isopropoxide of 2.4 to 2.6.

2. The titanium containing catalyst according to claim 1, which is a solution or a solid.

3. A composition comprising the titanium containing catalyst according to claim 1 and at least one of a co-catalyst, a toner, a phosphorous compound, a scavenger, a dulling agent, a reheat additive or mixtures of two or more of the same or different aforementioned compounds.

4. The titanium containing catalyst according to claim 1, wherein the sum of all titanium oxide species relative to the sum of all titanium alpha-hydroxy carboxylate species is less than 0.60 mol.-%.

5. The titanium containing catalyst according to claim 1, wherein the sum of all titanium oxide species relative to the sum of all titanium alpha-hydroxy carboxylate species is less than 0.30 mol.-%.

6. The titanium containing catalyst according to claim 1, wherein the sum of all titanium oxide species relative to the sum of all titanium alpha-hydroxy carboxylate species is less than 0.01 mol.-%.

\* \* \* \* \*